(12) United States Patent
Hiratsuka et al.

(10) Patent No.: US 7,052,653 B2
(45) Date of Patent: May 30, 2006

(54) MICROSIZE DRIVING DEVICE AND METHOD FOR PREPARATION THEREOF

(75) Inventors: Yuichi Hiratsuka, Tsukuba (JP); Taro Uyeda, Tsukuba (JP); Tetsuya Tada, Tsukuba (JP); Toshihiko Kanayama, Tsuchiura (JP)

(73) Assignee: Japan as represented by the Secretary of Agency of Industrial Science and Technology, Tokyo-to (JP)

( * ) Notice: Subject to any disclaimer, the term of this patent is extended or adjusted under 35 U.S.C. 154(b) by 1119 days.

(21) Appl. No.: 09/748,161

(22) Filed: Dec. 27, 2000

(65) Prior Publication Data

US 2004/0071607 A1   Apr. 15, 2004

(30) Foreign Application Priority Data

Jul. 10, 2000   (JP) .............................. 2000-208632

(51) Int. Cl.
*B01J 10/00* (2006.01)
*B01J 10/02* (2006.01)
*B01J 12/00* (2006.01)
*B01J 12/02* (2006.01)
*B01J 14/00* (2006.01)

(52) U.S. Cl. ...................................... 422/129; 530/350

(58) Field of Classification Search ................ 530/350; 422/129
See application file for complete search history.

(56) References Cited

OTHER PUBLICATIONS

Hiratsuka et al., 2000 International Microprocesses and Nanotechnology Conference, Molecular Circulator Driven by Motor Proteins, Sponsered by The Japan society of Applied Physics, pp. 296-297.*
Suzuki et al., Japanese Journal of Applied Physics, vol. 34, Part 1, No. 7B, pp. 3937-3941 (1995).
Suzuki et al., Biophysical Journal, vol. 72, pp. 1997-2001 (1997).
Kron et al., Proceedings of National Academy of Science, U.S.A., vol. 83, pp. 6272-6276 (1986).
Vale et al., Cell, vol. 42, pp. 39-50 (1985).
Nicolau et al., Biophysical Journal, vol. 77, pp. 1126-1134 (1999).

* cited by examiner

*Primary Examiner*—Jon Weber
*Assistant Examiner*—Robert B. Mondesi
(74) *Attorney, Agent, or Firm*—Wenderoth, Lind & Ponack, L.L.P.

(57) ABSTRACT

Disclosed is a microsize driving device in which falling of track proteins from an arrangement of motor protein molecules arranged on a linear track groove provided on a substrate is suppressed and utilization of kinetic energy of track proteins as a driving energy is made possible by controlling the moving direction to a single direction. Namely, provided is a microsize driving device which comprises a substrate, an arrangement of motor protein molecules such as, for example, kinesin molecules deposited on the bottom of a linear track groove provided thereon and track proteins such as, for example, microtubules disposed thereon and is characterized in that the said linear track groove has side surfaces shaped in such a structure as to permit a linear movement of the track proteins moving in a certain specific direction but to inhibit the track proteins moving in the reverse direction thereto causing reversion for the movement in the above mentioned specific direction.

9 Claims, 3 Drawing Sheets

MICROSIZE DRIVING DEVICE AND METHOD FOR PREPARATION THEREOF

BACKGROUND OF THE INVENTION

The present invention relates to a novel microsize driving device utilizable for transportation of microsize materials or so as a linear driving device or a rotary driving device within a micrometer-order region as well as to a method for the preparation thereof.

A protein which is found in a living body and exhibits mobility function in itself, such as kinesin and myosin, is generally called a motor protein. Kinesin and myosin have an ability to drive fibrous proteins such as microtubules and actin along the fibrous axis thereof by utilizing the energy released when adenosine triphosphate (referred to as ATP hereinafter) is hydrolyzed. These fibrous proteins capable of moving are defined here as a track protein.

While kinesin and myosin have a molecular weight of 140 kDa and 500 kDa, respectively, the size of the force generating domains is very small to be 4×5 nm and 5×20 nm, respectively. In microtubules and actin, the fibrous structure is formed by the self-assembly of molecules having a diameter of several nm so that fibers having a length of several tens of micrometers can be formed by causing self-assembly of these molecules in vitro.

As to such motor protein molecules, it is known that movements in random directions are effected when they are adsorbed on the whole surface of a substrate and track proteins are disposed thereon and linear bilateral movements are caused when they are arranged on a linearly patterned layer of a fluorocarbon resin or methacrylic acid-based resin and track proteins are disposed thereon (see Japanese Journal of Applied Physics, volume 34, 1995, pages 3937–3941; Biophys. J., volume 72, 1997, pages 1997–2001; Proc. Natl. Acad. Sci., U.S.A., volume 83, 1986, pages 6272–6276 and Cell, volume 42, 1985, pages 39–50).

FIG. 1 is a schematic perspective illustration of a state in which a track 2 formed as a raise on a substrate 1 is provided with an arrangement layer 3 of such motor protein molecules and track proteins 4 are disposed further thereon.

It could be expected that, if the energy of movement generated between such a motor protein and a track protein could be taken out, the same could be utilized, for example, as a power source for transportation of a microsize body but two problems must be solved therefor.

The first problem is to inhibit disappearance of the track proteins disposed on the arrangement of the motor protein molecules arranged within the track 2 on the substrate 1. Namely, while it is the prior art that, as is shown in FIG. 1, the motor protein molecules are adsorbed on the tracks 2 formed from a fluorocarbon resin or a (meth)acrylic acid-based resin, these tracks 2 are formed as a raise on the substrate 1 so that the track proteins 4 disposed thereon eventually fall from the track 2 during movements unavoidably resulting in a decrease of the amount thereof in the lapse of time. Accordingly, it is essential to accomplish an improvement in order to maintain the movement with stability within the tracks 2 over a long time.

The second problem is how to control the moving direction of the track proteins. When the motor protein molecules are arranged on a linear track and the track proteins are disposed thereon by a conventional method, namely, the movement of the track proteins is in bilateral directions along the lengthwise direction of the track so that the kinetic energy of the individual molecules cannot be taken out for utilization as a driving power source due to cancellation among the individual molecules. It is accordingly necessary to control the movement in a single direction in order to accomplish utilization of the kinetic energy as a driving power source.

Absolutely no reports are available heretofore, however, on the attempts to solve the above mentioned two problems for track proteins to be driven by motor protein molecules.

SUMMARY OF THE INVENTION

The present invention has been completed with an object to inhibit falling of the track proteins from the arrangement of the motor protein molecules on a track provided on a substrate and to enable utilization of the kinetic energy of the track proteins as a driving power source by controlling the moving direction thereof.

The inventors have continued extensive investigations for developing a method to utilize the kinetic energy produced by the arrangement of motor protein molecules and moving track proteins disposed thereon and, as a result thereof, have arrived at a discovery that the object can be accomplished by forming the linear track provided on a substrate in a configuration of a groove with deposition of the motor protein molecules on the bottom portion only thereof and by shaping the side surfaces of the groove in such a structure as to permit movement of the track proteins moving in a specific direction (referred to hereinafter as the normal direction) but to inhibit the track proteins moving in a direction reversed thereto (referred to hereinafter as the reverse direction) causing reversion for the movement into the normal direction leading to completion of the present invention on the base of this discovery.

Namely, the microsize driving device provided by the present invention comprises:

(a) a substrate having a linear track groove;
(b) an arrangement of motor protein molecules deposited on the bottom of the linear track groove; and
(c) track proteins disposed on the arrangement of the motor protein molecules, the said linear track groove having a side surface shaped in such a structure as to permit the linear movement of the track proteins moving in a specific direction but inhibit the track proteins moving in a direction reverse to the specific direction causing reversion for the movement in the above mentioned specific direction.

The method for the preparation of the microsize driving device provided by the present invention comprises the steps of:

(A) forming a pattern of a linear track by providing a photoresist layer on a substrate and patternwise exposing the same to light through a photomask followed by development;
(B) removing the photoresist layer remaining on the light-exposed areas of the substrate by a plasma treatment or sputtering to form a linear track groove;
(C) injecting a liquid containing a motor protein into the linear track groove to have the motor protein molecules deposited on the bottom thereof forming a molecular arrangement; and
(D) disposing track proteins on the molecular arrangement.

DETAILED DESCRIPTION OF THE PREFERRED EMBODIMENTS

Figure 1:
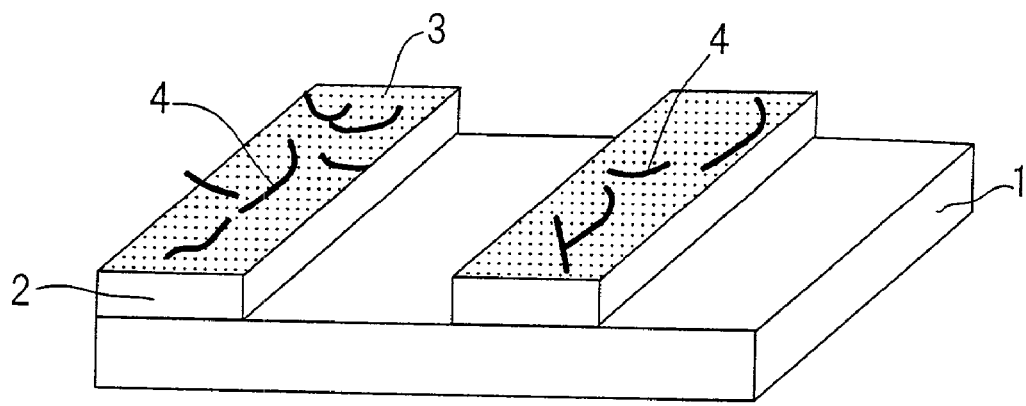
FIG. 1 is a perspective view schematically showing the performance of a motor protein and a track protein in the prior art.
Figure 2:
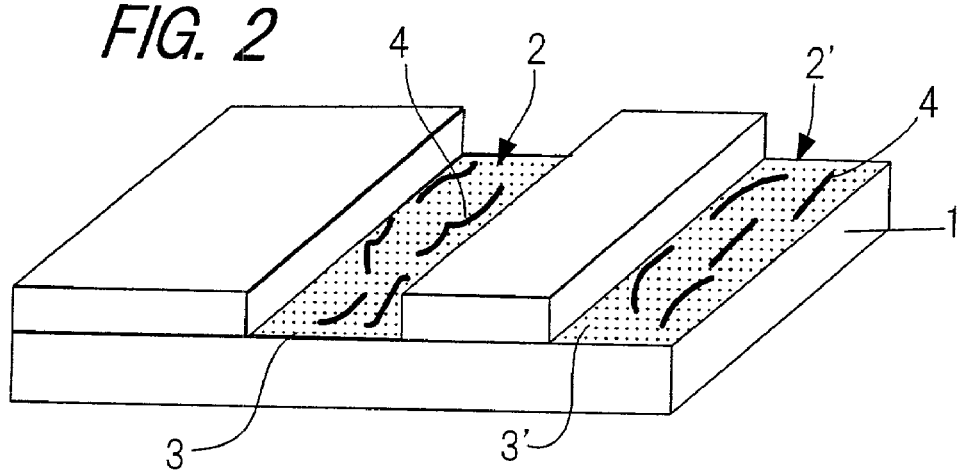
FIG. 2 is a perspective view schematically showing the structure of the track groove in the microsize driving device according to the present invention.
Figure 3:
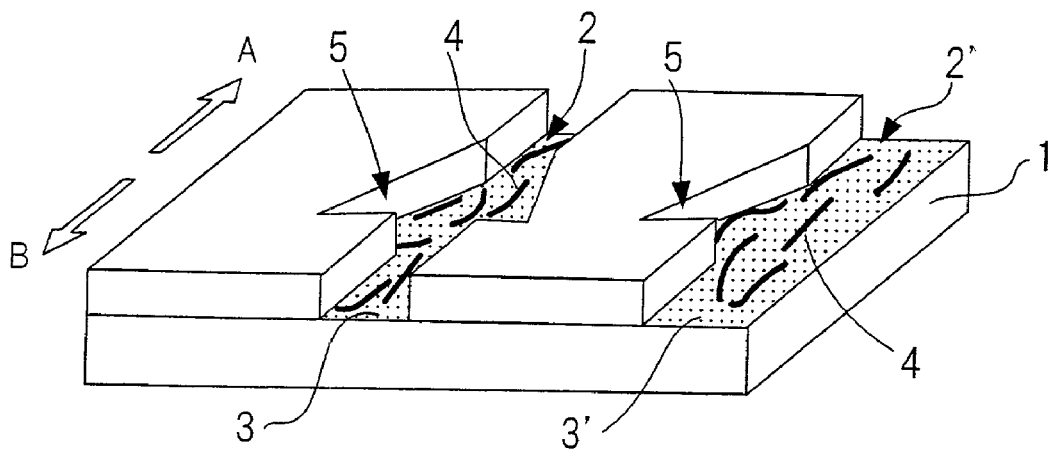
FIG. 3 is a perspective view showing an example of the inventive microsize driving device having a notch in the side surface of a track groove.

In the following, examples of the embodiments of the present invention are described by making reference to the accompanying drawing. FIG. 2 is a perspective view schematically showing the structure of the linear track groove in a microsize driving device of the present invention and FIG. 3 is a perspective view of an example in which the linear track groove is formed to have a configuration of the side surface to permit the linear movement of the track proteins moving in a specific direction but to inhibit the track proteins moving in a direction reverse to the said specific direction causing reversion for the movement in the specific direction.

In these figures, the motor protein molecules are deposited over the whole surface onto the bottom surfaces of the track grooves 2,2' provided on the substrate 1 to form molecular arrangements 3,3' and the track proteins 4, ... are disposed thereon. In FIG. 3, the track grooves 2,2' are provided with wedge-formed notches 5,5 on both of the respective side surfaces so as to permit movement of the track proteins 4, ... in the direction indicated by the arrow mark A (normal direction) but to inhibit the movement in the reverse direction indicated by the arrow mark B (reverse direction) causing reversion toward the normal direction.

Figure 4A:
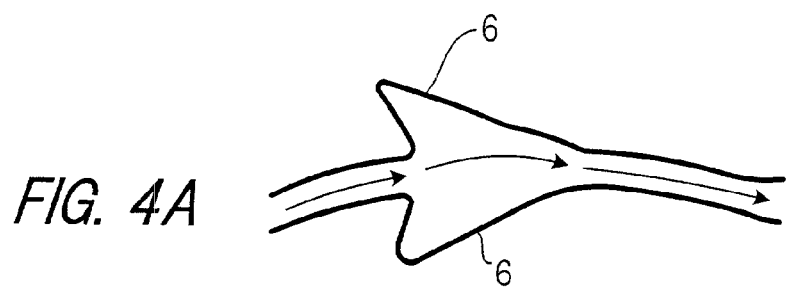
FIG. 4A and FIG. 4B are each an explanatory illustration showing the movement of track proteins in the normal direction and reverse direction, respectively, in the present invention.
Figure 4B:
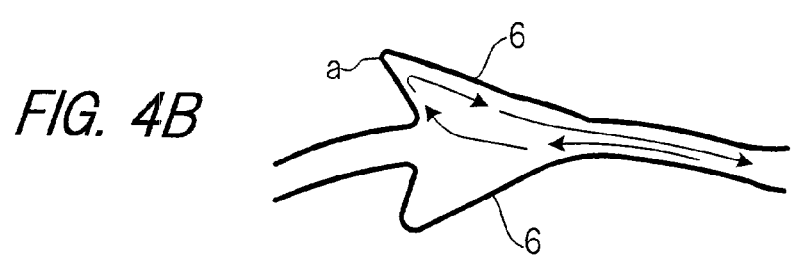

FIGS. 4A and 4B are each an explanatory illustration showing the behavior of the track proteins in which the side surfaces 6,6 of the linear track groove 2 are shaped in such a wedge-like notched form that the width of the track groove 2 is broadened from right to left or, in other words, narrowed from left to right. While the track proteins proceeding from left to right along the arrow mark in FIG. 4A can smoothly move along the arrow mark, the track proteins proceeding from right to left move along the arrow mark in FIG. 4B and hit at the bottom a of the wedge-formed notch to be inhibited from proceeding causing reversion for the movement from left to right. As a result thereof, the track proteins under bilateral movements by means of the motor protein molecules arranged on the bottom surface of the linear track groove 2 enter the movement in a specific single direction or, namely, in the direction from left to right in FIGS. 4A and 4B.

Figure 5A:
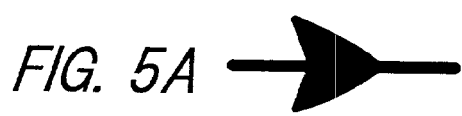
FIG. 5A to FIG. 5G are each a plan view showing an example of the profiles of the side surface of the track groove in the present invention.
Figure 5E:
Figure 5B:
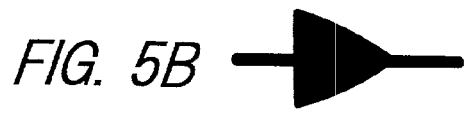
Figure 5C:
Figure 5F:
Figure 5D:
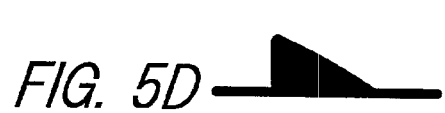
Figure 5G:

FIGS. 5A to 5G are each a plan view of an example of the pattern profiles provided in the linear track groove shaped in such a fashion that the width of the track is narrowed along the direction from left to right and broadened in the reverse direction. The profile of the rectifying part is not limited thereto but a great number of modifications besides them are possible. Each of the patterns in FIGS. 5A to 5G rectifies the movement of the track proteins to the direction from left to right in the same manner as in the pattern of FIG. 4. As to the dimensions of the pattern there, the rectifying effect on the movement direction can be exhibited with higher efficiency when the width of the entering side of the track proteins is larger than the length of the track protein in the lengthwise direction with a narrowed exit opening. In the pattern of FIG. 5G, the direction along which the track proteins enter the rectifying part and the direction along which they come out from the rectifying part are not on the same straight line. In such a case, it is rarely the case that the track proteins reversedly running from the exit side get out directly from the inlet so as to exhibit a further improved rectifying effect on the moving direction.

For the substrate in the microsize driving device of the present invention, metals such as silicon, aluminum, tantalum, titanium and the like, glass materials such as silicate glass and the like, fluorocarbon resins such as polytetrafluoroethylene, copolymers of tetrafluoroethylene and hexafluoropropylene, copolymers of tetrafluoroethylene and perfluoro(ethenylalkyl ether), copolymers of poly(monochloro trifluoro ethylene) tetrafluoroethylene and ethylene and the like, acrylic acid-based resins such as polymethyl methacrylate, copolymers of methyl acrylate and methyl methacrylate, copolymers of ethyl acrylate and methyl methacrylate and polystyrenes can be used. As the material of the substrate, it is preferable to use one selected from those having affinity with the motor protein molecules to be used and capable of being readily bonded thereto.

As the motor protein in the inventive microsize driving device, kinesin, myosin and the like can be used. It is desirable that these proteins are improved beforehand in order to facilitate attaching to the track groove. Such an improvement can be accomplished by the method of, for example, genetic engineering modification of the properties of the motor protein per se or by the method in which the motor protein is biochemically labeled with biotin and attached to the track groove with intervention of streptoavidin.

As the track protein used in the inventive microsize driving device, fibrous proteins such as microtubules and actin are preferable.

It is preferable that the linear track groove in the inventive microsize driving device has side surfaces formed of a material to which the motor protein molecules used can attach with difficulty. Such a material includes, for example, melamine-based resins and (meth)acrylic acid ester-based resins.

As is described below, the microsize driving device of the present invention can be advantageously prepared by utilizing the photolithographic technology. In the following, the preparation method is described by way of an example utilizing silicate glass for the substrate, kinesin as the motor protein and microtubules as the track protein.

A layer of a melamine-based or (meth)acrylic acid ester-based photoresist is formed in a thickness of about 1 μm on a silicate glass substrate and a pattern of a linear track groove is formed by image-forming light-exposure through a photomask followed by development. In the next place, while it is necessary to bring a kinesin solution into contact with the linear track groove to have the kinesin adsorbed to the glass plate, mere contacting of the solution is not sufficient for the formation of an arrangement due to random adsorption of the kinesin molecules on either of a glass surface and resin surface.

While adsorption of kinesin on the linear track groove has a bilateral nature of hydrophobic bonding and ionic bonding, resin surfaces are hydrophobic and glass surfaces are ionic so that the difference between these natures can be utilized for the preferential adsorption onto the glass surfaces only. Namely, kinesin molecules can be adsorbed onto the glass surface only by inhibition of adsorption onto the resin surface when a non-ionic surface active agent is added to the kinesin solution to be brought into contact with the glass substrate. Preferable non-ionic surface active agents used here include alkylaryl polyethyleneglycols, polyoxyethylene sorbitan monopalmitates, lauryl alcohol-polyethyleneoxide adducts and the like. Within the linear track groove obtained in this way, the microtubules enter a very stable movement to exhibit a movement constrained to the track over several hours or longer.

Other motor proteins, such as, for example, myosin, exhibit different behaviors to the material of the substrate. It is a possible way in such a case to effect genetic engineering modification so as to change the bonding characteristic to be similar to that of kinesin so that the inventive device can be prepared by the same method even by the use of a motor protein other than kinesin. Needless to say, it is not necessary to effect modification of the motor protein when a substrate material having adaptability to the motor protein to be used is selected.

In the above described method, the adsorptivity of the motor protein molecules to the substrate can be effectively enhanced by completely removing the photoresist film remaining on the substrate after the development treatment. The method for the removal of the resist film includes an oxygen plasma etching treatment and a sputtering treatment with an inert gas.

Figure 6:
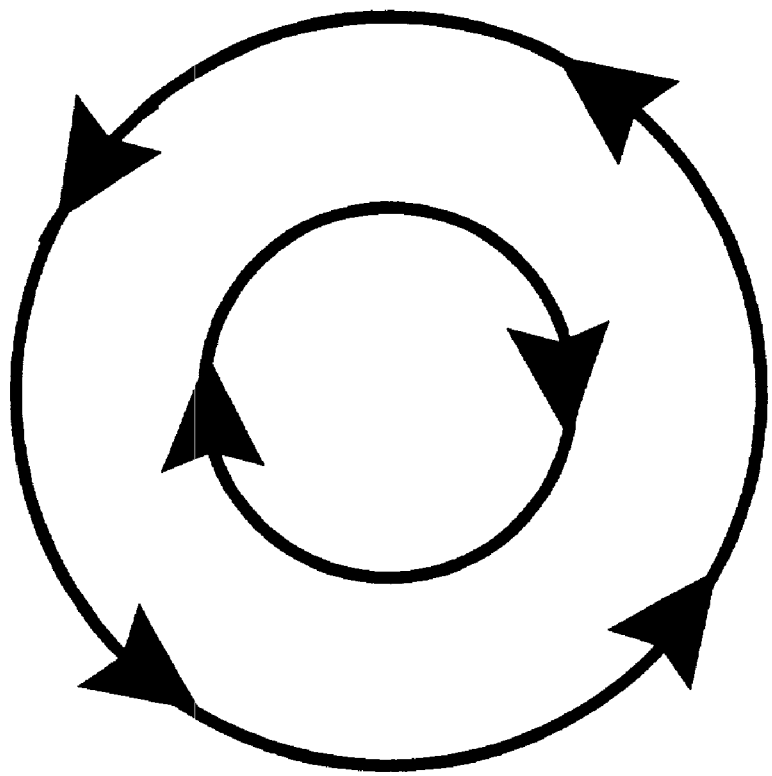
FIG. 6 is a plan view showing an example of the case where the linear track groove in the present invention has a circular ring form.

As is shown in FIG. 6, a rotary driving device, in which the track proteins move in a single direction only, can be obtained by forming the linear track groove in the microsize driving device of the present invention in a ring form.

By using the microsize driving device obtained in this way, an ultrafine particle of glass or polystyrene can be transported as bonded to the track proteins. When a microsize driving device having a track groove shaped in a circular form is employed, a gear can be rotated by connecting the gear bonded to the track proteins onto the circle. Furthermore, a body can be transported in a microsize space as supported on the track proteins by forming two domains in which the track proteins are freely movable and connecting them with a linear track capable of rectification therebetween.

In the following, the present invention is described in more detail by way of Examples.

EXAMPLE 1

A silicate glass plate as the substrate was coated by spin coating with a negative-working photoresist solution (commercial product SAL 601, a melamine resin-based photoresist composition produced by Shipley Co.) put thereon in drops to form a coating film having a thickness of 1 μm after drying. After drying, the coating film was patternwise light-exposed through a photomask and developed by using a developer solution (MICROPOSIT Developer MF-312, commercial name by Shipley Co.) to form a groove-formed track pattern having a width of 2 μm, length of 500 μm and depth of 1 μm on the substrate surface.

After drying of the substrate as developed, a solution prepared by dissolving, in a buffer solution containing 0.1% of a non-ionic surface active agent (Triton X100, a comercial name by Rohm & Haas Co., alkylaryl polyethyleneglycol), 50 mM of potassium acetate, 10 mM of tris acetic acid (pH 7.5), 4 mM of magnesium sulfate, 1 mM of ethyleneglycol bis(2-aminoethyl ether) tetraacetic acid, 7 mM of 2-mercaptoethanol and 25 μg/ml of casein, kinesin in a concentration of 5 μg/ml or 10 μg/ml was put in drops onto the track groove and kept standing at room temperature for 2 minutes in an attempt to deposit the kinesin molecules onto the glass substrate but an arrangement of the kinesin molecules could be obtained in neither of the resin surface and glass surface.

The same procedure as described above was repeated, therefore, except that the substrate surface was beforehand subjected to an oxygen plasma etching treatment under the conditions of the oxygen flow rate of 150 ml/minute and high frequency electric power of 280 watts for 60 seconds to obtain an arrangement of the kinesin molecules preferentially deposited onto the glass surface only without deposition of kinesin on the resin surface.

A solution of microtubules was put in drops onto the linear track groove obtained in this way to have the microtubules bonded to kinesin followed by the addition of ATP to initiate movement of the microtubules so that the microtubules entered movement along the wall of the track within the track groove and continued a bilateral reciprocating movement with conversion of the direction at a probability of approximately 100% without running off the track.

EXAMPLE 2

A glass substrate was coated by the spin coating method with a methacrylic acid ester resin-based positive-working photoresist solution put thereon in drops to give a film thickness of 1 μm after drying and dried at 170° C. for 10 minutes. After a patterning light-exposure to light of 254 nm wavelength through a photomask, development was conducted by using methyl isobutyl ketone. As a result, the light-exposed areas were removed to form a track groove which was similar to Example 1. This substrate was subjected to oxygen plasma etching and a kinesin solution containing a non-ionic surface active agent was put thereon in drops to have the kinesin adsorbed. Kinesin was preferentially adsorbed on the glass surface of the substrate without adsorption onto the resin surface. Microtubules and ATP were added to the substrate surface by using the same method as in Example 1 so that the movement of the microtubules could be limited within the track groove and the movement was a bilateral movement along the linear track groove.

COMPARATIVE EXAMPLE

An arrangement of kinesin molecules was formed on a glass substrate in the same method as in Example 1 excepting for the formation of the track grooves in double rings having a width of 1.5 to 2.5 μm and a radius of 60 μm or 30 μm and microtubule molecules were disposed thereon to be put into movement. The thus obtained movement of the microtubules was a clockwise and counterclockwise bilateral rotary movement along the circular track grooves but the direction of revolution could not be controlled.

EXAMPLE 3

Arrangement of kinesin molecules was undertaken and microtubules were brought into rotary movement by the same method as in Comparative Example except that, though being the same circular pattern as in the above described Comparative Example, dual ring-formed track grooves having wedge-formed notches in the side surfaces as is illustrated in FIG. 6 were formed on the substrate with an object to control the direction of the rotary movement of the microtubules. The direction of the rotary movement of the microtubules was in perfect coincidence with the direction intended by the rectifying pattern. In this way, the movement of the microtubules could be controlled to be counterclockwise on the outer side circular track groove and clockwise on the inner side circular track groove.

EXAMPLE 4

In order to evaluate performance of the rectifying patterns, an attempt of numerical evaluation of the rectifying efficiency was made for the four different patterns illustrated in FIGS. 5A, 5B, 5C and 5D. Actual measurements were undertaken in the cases where the entering direction of the microtubules into the rectifying pattern was in the normal direction and in the cases in the reverse direction for the s value (normal direction) and t value (reverse direction) as the probability of the cases where the microtubules passed the rectifying pattern without reversion of the direction. A smaller s value means that the rectifying effect is more reliable. The results thereof were that, while the t value was 1.00 in each case, the s value was 0.27, 0.42, 0.59 and 0.82, respectively, to find that the rectifying effect of the rectifying pattern of FIG. 5D was not good. Namely, it was understood that an outstandingly high rectifying efficiency was exhibited by the rectifying pattern of FIG. 5A among these four kinds of the rectifying patterns.

EXAMPLE 5

Figure 7:
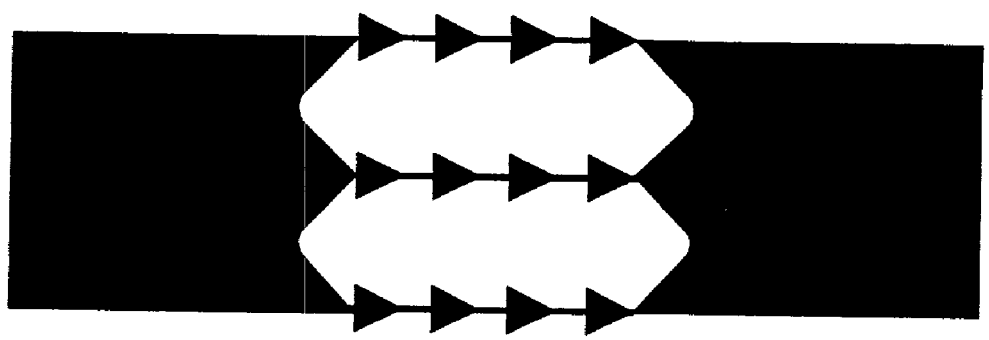
FIG. 7 is a plan view showing the profile of the side surface of the track groove used in Example 5.

Microtubules were labeled with biotin by using succinimide labeled with biotin. Polystyrene beads of 1 μm diameter were coated with bovine serum albumin labeled with biotin and further admixed with streptoavidin for bonding to the bovine serum albumin labeled with biotin so as to label the surface of the beads with streptoavidin. Since streptoavidin has four biotin-binding sites per molecule, the surface of the beads was imparted with a possibility of further bonding of biotin. Accordingly, the beads labeled with streptoavidin could be bonded to the microtubules labeled with biotin. By causing adsorption of such microtubules onto the substrate having an arrangement of kinesin molecules in a pattern of FIG. 7, the beads could be transported by the microtubules within the pattern.

What is claimed is:

1. A microsize driving device which comprises:
   (a) a substrate having a linear track groove;
   (b) an arrangement of motor protein molecules deposited on the bottom of the linear track groove; and
   (c) track proteins disposed on the arrangement of the motor protein molecules,
   the linear track groove having side surfaces shaped in a moving direction controlling structure which permits a linear movement of the track proteins moving in a specific direction but inhibits the track proteins moving in a direction reverse to the said specific direction to cause reversion for the movement in the said specific direction.

2. The microsize driving device as described in claim 1 in which the moving direction controlling structure is a patterned structure of which, in a part of the side surfaces of the linear track groove, the track has a width narrowing toward the specific direction and broadening toward the reversed direction.

3. The microsize driving device as described in claim 2 in which the linear track groove is provided in the intermediate position with a part of which one end has a width broader than the lengthwise length of the track protein and the other end has a width narrower than the same.

4. The microsize driving device as described in claim 1 in which the moving direction controlling structure of the linear track groove has a forward portion and a rearward portion which are not on a single straight line.

5. The microsize driving device as described in claim 1 in which the bottom of the linear track groove is formed from silicate glass or polystyrene.

6. The microsize driving device as described in claim 1 in which the linear track groove has a side wall made from a melamine-based resin or a (meth)acrylic acid-based resin.

7. The microsize driving device as described in claim 1 in which the motor protein is kinesin or myosin.

8. The microsize driving device as described in claim 1 in which the track protein is microtubule or actin.

9. The microsize driving device as described in claim 1 in which the linear track groove has a ring-formed pattern.

* * * * *